United States Patent [19]

Naftilan et al.

[11] Patent Number: 5,635,380
[45] Date of Patent: Jun. 3, 1997

[54] ENHANCEMENT OF NUCLEIC ACID TRANSFER BY COUPLING VIRUS TO NUCLEIC ACID VIA LIPIDS

[75] Inventors: Allen J. Naftilan; Rampyari Walia, both of Nashville, Tenn.

[73] Assignee: Vanderbilt University, Nashville, Tenn.

[21] Appl. No.: 183,055

[22] Filed: Jan. 18, 1994

[51] Int. Cl.$^6$ .......................... A61K 48/00; C12N 15/00
[52] U.S. Cl. ................................. 435/172.3; 435/320.1; 435/172.1; 424/450; 424/86.2
[58] Field of Search .......................... 435/172.1, 172.3, 435/240.1, 240.2, 240.4, 320.1; 514/44; 935/54, 56, 57; 424/450, 85.2

[56] References Cited

U.S. PATENT DOCUMENTS 4,897,355   1/1990   Eppstein et al. .................. 435/240.2

OTHER PUBLICATIONS

Ryuichi Morishita et al., "Novel In Vitro Gene Transfer Method for Study of Local Modulators in Vascular Smooth Muscle Cells," *Hypertension*, 21(6):894–899 (Jun. 1993).

Richard J. Cristiano et al., "Hepatic Gene Therapy: Adenovirus Enhancement of Receptor–Mediated Gene Delivery and Expression in Primary Hepatocytes," *Proc. Natl. Acad. Sci. USA*, 90:2122–2126 (Mar. 1993).

L. Gao et al., "Direct In Vivo Gene Transfer to Airway Epithelium Employing Adenovirus–Polylysine–DNA Complexes," *Human Gene Therapy*, 4:17–24 (1993).

Kunihiko Yoshimura et al., "Adenovirus–Mediated Augmentation of Cell Transfection with Unmodified Plasmid Vectors," *The Journal of Biological Chemistry*, 268(4):2300–2303 (1993).

Cynthia L. Innes et al., "Cationic Liposomes (lipofectin) Mediate Retroviral Infection in the Absence of Specific Receptors," *Journal of Virology*, 64(2):957–961 (Feb. 1990).

Yasufumi Kaneda et al., "Increased Expression of DNA Cointroduced with Nuclear Protein in Adult Rat Liver," *Science*, 243:375–378 (Jan. 20, 1989).

Culver et al., TIG, 1994, 10(5), 174–178.

Marshall, Science, 269, 1995, 1050–1055.

Miller et al., FASEB. J., 9, 1995, 190–199.

Hodgson, Exp. Opin. Ther. Pat., 1995, 5(5), 459–468.

Yoshimura. K. et al. "Advenovirus–mediated augmentation of cell transfection with unmodified plasmid vectors," JBC 268(4):2300–2303 (1993).

Life Technologies Inc., Gaithersburg MD "1993–1994 Catalog" pp. 9–19 (1993).

Georges, R.N. et al. "Prevention of orthotopic human lung cancer growth by intratrachael instillation of a retroviral antisense k–ras construct" Cancer Research 53:1743–46 (1993).

Leibiger, B. et al. "Expression of exogenous DNA in rat liver cells after liposome–mediated transfection in vivo," BBRC 174(3):1223–1231 (1991).

Gao, L. et al. "Direct in vivo gene transfer to airway epithelium employing adenovirus–polylysine–DNA complexes," Human Gene Therapy 4:17–24 (1993).

*Primary Examiner*—Jacqueline M. Stone
*Assistant Examiner*—Andrew Milne
*Attorney, Agent, or Firm*—Needle & Rosenberg, P.C.

[57] ABSTRACT

This invention provides a method of enhancing the delivery of a nucleic acid into a cell, wherein a complex is formed comprising the nucleic acid, a cationic liposome, and a replication-deficient adenovirus, and the complex is administered to the cell to thereby enhance delivery of the nucleic acid into the cell. The method can be used to deliver the nucleic acid into a cell in a subject by administering the above complex into the subject.

10 Claims, No Drawings

ENHANCEMENT OF NUCLEIC ACID TRANSFER BY COUPLING VIRUS TO NUCLEIC ACID VIA LIPIDS

ACKNOWLEDGEMENTS

This invention was made with government support under Grant Nos. HL 43052 and HL 47152 awarded by The National Institutes of Health. The United States government has certain rights in the invention.

BACKGROUND OF THE INVENTION

1. Field of the Invention

The present invention relates to a method of enhancing the delivery of a nucleic acid into a cell. In particular are provided methods comprising forming a complex of a nucleic acid, a cationic liposome and a virus and administering the complex to the cell to enhance delivery of the nucleic acid to the cell. Also provided are complexes comprising a nucleic acid, a cationic liposome and a virus.

2. Background Art

Transfer of genes into cells and expression of the transferred genes therein has been a subject and goal of much study, with limited success. Several different methods have been reported in the literature for gene transfer in vitro and/or in vivo, some using viruses and/or liposomes.

The use of liposomes, and in particular, cationic liposomes, for gene transfer has been described in vitro (e.g., Ciccarone, V., et al., *Focus*, 15(3):73–83 (1992)). However, the efficiency of transfer recited in the literature has not been as high as desirable for effective gene therapy and has only been performed in a limited number of cell types.

Retroviruses have been administered in vitro with cationic liposomes to infect cultured cells and thus deliver the DNA of the retroviruses to the cells (Innes et al., *J. Virol.*, 64(2):957–961 (1990)). Such a method requires insertion of the nucleic acid to be expressed into the viral genome, and further, viral genes are co-introduced into the target cells. Sendai virus (hemagglutinating virus of Japan (HVJ)) has been utilized wherein anionic or neutral liposomes encase a plasmid of choice, the plasmid-containing liposomes are then complexed with inactivated HVJ, and the liposome-HVJ complex is incubated with vascular smooth muscle cells to cause expression of the plasmid in the cells (Morishita et al., *Hypertension*, 21:894–899 (1993)). Forming these neutral or anionic liposomes that encase the DNA requires additional methods such as reverse-phase evaporation of various lipids, DNA, and any additional desired components of the liposomes, which method uses organic solvents (Kaneda, et al., *Science*, 243:375–378 (1989)). Additionally, the efficiency of these gene transfer methods is not very high.

Adenoviruses have also been utilized for gene transfer methods. Many of these methods, however, require the synthesis of a variety of molecular conjugates and/or the efficiency of transfer has not been as high as desired for effective gene therapy. Gao et al., *Human Gene Therapy*, 4:17–24 (1993) provides a method of in vivo delivery of genes to respiratory epithelium. This method requires the synthesis of two molecular conjugates, an adenovirus-polylysine conjugate joined by an antibody or chemical bridge and a DNA-polylysine conjugate, which are then complexed together to form an adenovirus-polylysine-DNA complex via the polylysine chains. This reference also disclosed the formation of a human transferrin-adenovirus-polylysine-DNA complex requiring the formation of different molecular conjugates which are then complexed together. Thus, Gao et al. creates a product having DNA linked to adenovirus via conjugation with polylysine without the use of liposomes.

Cristiano et al., utilizes adenovirus for gene delivery by forming an asialoorosomucoid (ASOR)-polylysine conjugate, which is then complexed with DNA. The method involves adding the complex to culture cells, followed immediately by the addition of replication-deficient adenovirus. The ASOR directs the complex specifically to hepatocytes. It is not clear whether a complex including the adenovirus can form in this in vitro method; however, if the method was repeated in vivo, because of the separate steps, the likelihood of complex formation would greatly decrease.

Yoshimura et al., describes a method wherein DNA and the cationic liposome LIPOFECTIN are complexed and then diluted. This diluted mixture is then added to cell cultures. Thirty minutes later, replication-deficient adenovirus is added to the cultures. Thus, the adenovirus is never complexed with the DNA. Furthermore, if the method were transferred to an in vivo use, also, no complex with the adenovirus could be formed because of the time lag. Such a method has been shown to provide some improvement in transfer efficiency in vitro.

It has been shown that empty adenoviral capsids bind double-stranded DNA (Gian, C. Z. and Tibbets, *J. Virol.* 32: 995–1005 (1979)).

The present invention provides the use of replication-deficient adenovirus-DNA-cationic liposome complexes. The efficiency of gene transfer using the present inventive method is very high compared to other methods of gene transfer using liposome-DNA complexes or DNA-polylysine complexes. Given the simplicity of the complexing protocol for DNA-lipid-virus complexes (no genetic manipulations, no synthesis of molecular conjugates, no toxicity to cells), it has a wide applicability for transfecting genes transiently in vitro or in vivo. It is also much simpler to perform than earlier methods. The method thus fills a need for high-efficiency gene transfer techniques that many have previously tried to solve with only limited success.

SUMMARY OF THE INVENTION

The present invention provides a method of enhancing the delivery of a nucleic acid into a cell, comprising forming a complex comprising the nucleic acid, a cationic liposome and a replication-deficient virus and administering the complex to the cell, thereby enhancing the delivery of the nucleic acid into the cell. The replication-deficient virus can be an adenovirus.

This invention further provides a method of enhancing the delivery of a nucleic acid into a cell in a subject comprising forming a complex of the nucleic acid, a cationic liposome and a replication-deficient virus and administering the complex to the subject, thereby enhancing the delivery of the nucleic acid into the cell. Additionally provided by the present invention is a method of transiently increasing the level of a protein deficient in a cell in a subject comprising forming a complex of a cationic liposome, an adenovirus and a DNA molecule functionally encoding the protein, and administering the complex to the subject, thereby delivering the DNA to the cell and transiently increasing the level of the protein encoded by the DNA in the cell.

The present invention also provides a method of enhancing the delivery of a nucleic acid to a cell in a subject comprising administering a complex comprising the nucleic acid, a cationic liposome and a replication deficient virus to the subject, thereby enhancing the delivery of the nucleic acid into the cell.

Also provided is a method of enhancing the delivery of a nucleic acid to a cell comprising administering a complex comprising the nucleic acid, a cationic liposome and a replication deficient virus to the cell, thereby enhancing the delivery of the nucleic acid into the cell.

Further, the invention provides complexes comprising a cationic liposome, a nucleic acid and a virus.

DESCRIPTION OF THE PREFERRED EMBODIMENTS

The present invention may be understood more readily by reference to the following detailed description of specific embodiments and the Examples and Tables included therein.

As used in the claims, "a" can mean one or more.

The present invention provides a method of enhancing the delivery of a nucleic acid, into a cell, comprising forming a complex comprising the nucleic acid, a cationic liposome and a virus and administering the complex to the cell, thereby enhancing the delivery of the nucleic acid into the cell. Delivery to a cell includes the nucleic acid being internalized to some area within the cell membrane, e.g., into a vesicle, the cytoplasm, an endosome, the nucleus, etc. By "enhancing" is included that a higher efficiency of delivery of a nucleic acid into a cell, which cell can be in a subject, can be obtained than with the nucleic acid alone (such as with standard methods as electroporation, calcium phosphate precipitation, etc.), the nucleic acid with liposomes alone, or the nucleic acid with virus alone. Additionally, the present method enhances gene delivery at a higher efficiency of transfer than previously known methods. The enhancement of gene transfer can occur by, for example, enhanced entry of the nucleic acid into the cell, mediated by both virus and liposomes, and due to virus causing lysis of the endosome, thereby preventing degradation of the nucleic acid (complexed with the virus) in the endosome.

The complex can be formed by mixing the nucleic acid with cationic liposomes and replication-deficient virus and allowing the complex to form. The mixing can occur, for example, in serum-free culture medium. The mixing can be performed at any desired temperature, with about 23° C. to about 42° C. being a preferred temperature range and with around 37° C. being an even more preferred temperature. Once complexing has occurred, other components, such as serum, can be added.

The nucleic acid can be a deoxyribonucleic acid (DNA) or a ribonucleic acid (RNA). If desired, the nucleic acid can functionally encode a peptide, a polypeptide or a protein. By "functionally" encodes is meant that the nucleic acid contains the nucleotide sequences necessary for the peptide, polypeptide or protein to be expressed in the cell, e.g., nucleotide sequences that allow for proper transcription of DNA into RNA and/or proper translation of RNA into an amino acid sequence. Such sequences can include an origin of replication for a plasmid, a promoter, an enhancer, and information processing sites, such as ribosome binding sites, RNA splice sites, polyadenylation sites, and transcriptional terminator sites. Useful promoters include the original promoter of a gene of interest, or promoters derived from, e.g., immunoglobulin genes, SV40, adenovirus, bovine papilloma virus or cytomegalovirus. Thus, by delivering a DNA or RNA that can be properly processed to create a peptide encoded therein, the peptide can be provided to a target cell. A ribonucleic acid can be, for example, an antisense RNA, either functionally encoded by a DNA delivered by this method or delivered directly as RNA by this method. Such replication constructs are known in the art, e.g., Sambrook, et al, 2d Ed. Cold Spring Harbor Laboratory Press, Cold Spring Harbor, N.Y. (1989).

The cationic liposome can be any cationic lipid mixture. Some commercially available cationic liposomes include, for example, LIPOFECTIN (DOTMA) (Gibco BRL, Gaithersburg, Md.), LIPOFECTAMINE (DOSPA) (Gibco BRL), LIPOFECTACE (GIBCO BRL) and DOTAP (Boehringer-Mannheim). A presently preferred liposome for in vitro use is LIPOFECTAMINE.

Any suitable desired virus can be used in this method. It is preferable that the virus chosen present minimal risk to the cells of adverse viral effects, particularly cell death. Therefore, preferable viruses include replication-deficient viruses. Some preferred viruses include adenoviruses, retroviruses, adeno-associated viruses, and Sendai viruses. Particularly preferred are adenoviruses, for example, the replication deficient strain Adenovirus 5 (AD5)-DL312 (Jones, N. and Shenk, T., Cell, 17:683–689 (1979); Shenk, T. et al., Cold Spring Harbor Symp. Quant. Biol. 44: 367–375 (1979)). The viruses can be rendered replication-deficient by any of several means known in the art. For example, the viruses can be inactivated by UV irradiation or psoralen, or genes necessary for replication can be deleted from the viral genome. (Cotten, M., et al., Proc. Natl. Acad. Sci. U.S.A. 89: 6094–6098 (1992); Shenk, T. et al., Cold Spring Harbor Symp. Quant. Biol. 44: 367–375 (1979))

Some replication-deficient adenoviruses, for example, have deletions of the E1A and E1B regions of the viral genome that are essential for viral replication. These viruses are attractive for use in gene therapy because they retain the gene delivery and the endosomal lysis ability of wild-type adenoviruses but cannot replicate in the cells that they infect. Furthermore, gene expression persists for a longer time because the adenovirus complexed with the DNA prevents the DNA from degrading in the lysosomes.

The virus chosen can depend upon the target cells or organ, particularly the specific receptors present on the surface of the target cells. Adenoviruses, for example, can infect a broad range of cell types from a variety of species, including humans, by fibers on their outer surface interacting with specific cell surface receptors (fiber receptors) on the target cell. However, because the present invention also requires the use of a cationic liposome (which facilitates cell membrane interaction), cells lacking a specific receptor for any selected virus can receive the transferred DNA.

Also provided herein is a method of enhancing the delivery of a nucleic acid into a cell in a subject, comprising forming a complex comprising the nucleic acid, a cationic liposome and a virus; and administering the complex to the subject, thereby enhancing the delivery of the nucleic acid into the cell. The virus can be chosen accordingly with the species of the subject and the particular cells, as noted above, or organ in the subject that it is desirable to provide with the nucleic acid. Adenovirus, for example, is useful for human subjects. Replication-deficient viruses are preferred, as discussed above.

The complex can be administered by any method that will cause the complex to come in contact with the desired target cells. The complex can be administered directly into the bloodstream, e.g., intravenously, intraarterially, intraventricularly, etc., or intramuscularly or subcutaneously. For example, the complex can be infused into a specific blood vessel in a subject for localized gene delivery, as by catheter. Likewise, inhalation administration can deliver the complex directly to the cells of the lung. Other types of administration are well known. (Remington's Pharmaceutical Sciences, E. W. Martin (ed.), Mack Publishing Co., Easton, Pa.)

Dosage will depend upon the amount of enhancement of delivery and/or expression of the nucleic acid desired, but can be readily determined by one of skill in the art based upon knowledge of the particular nucleic acid and upon the teachings set forth in the examples. The dosage optimization as set forth in the in vitro experiments can be used to determine an appropriate in vivo dose. Additionally, the dosages set forth for the dog and mouse in vivo experiment can be used to determine a human dose based on dose per target tissue/organ weight. Generally, the dosage will be similar or less than the amount provided in the dog experiments, and at the same proportion of components as provided in the in vivo experiments. The dosage will vary according to the purpose of providing the nucleic acid. For example, expression of a protein deficient in the subject will likely require a higher dose than if, for example, a tumor or organ is being targeted for delivery of a nucleic acid. The exact dosage can vary from subject to subject, depending upon the species, age, weight and general condition of the subject, as well as the severity of any condition to be treated by the administration, the particular nucleic acid being administered, the mode of administration, and the like.

The present invention is more particularly described in the following examples which are intended as illustrative only since numerous modifications and variations therein will be apparent to those skilled in the art.

Statement Concerning Utility

The utility of enhanced delivery of a nucleic acid is apparent from the above description. A few examples of such utility follow. Enhanced delivery can be used to increase the expression of a protein deficient in a cell for gene therapy. Enhanced delivery can also be used as a tool to study the effects of expression of proteins in cells. This enhanced delivery can also be used to study the cell or tissue infectivity distribution of expressed proteins. In addition, expression of nucleic acids can be used, as in the case of antisense RNA, to block the expression of an over expressed protein or block the replication of a virus. Further, enhanced delivery can be utilized to increase the transfection efficiency to host cells to increase expression of beneficial peptides, polypeptides and proteins.

EXAMPLES

Replication-deficient adenovirus strain Ad5 DL312 (Ad) was a kind gift from Dr. Tom Shenk (Princeton University, Princeton, N.J.). The virus was propagated in 293 (human embryonic kidney) cells grown in Minimal Eagle's Medium supplemented with 10% horse serum and purified by banding in CsCl gradients. The concentration of virus was determined using spectrophotometric analysis (One optical density unit at 260 nms=$10^{12}$ viral particles). The viral preparations were diluted with Opti-MEM 1 (from GIBCO BRL, Gaithersburg, Md.) and stored at −70° C.

HeLa cells, bovine aortic endothelial cells, cardiac myocytes and Cos 1 cells were maintained in Dulbecco's Modified Eagle's Medium supplemented with 10% fetal bovine serum and used for in vitro studies. The cationic lipids LIPOFECTIN and LIPOFECTAMINE were purchased from GIBCO BRL.

Transfection/Infection of Cells With DNA-Lipid-Adenovirus Complexes

A plasmid construct (RSV-luc) encoding the luciferase gene under control of the Rous sarcoma virus LTR (long terminal repeat region) was used in in vitro studies to assess the efficiency of gene transfer. A plasmid construct with beta galactosidase as a reporter gene under control of the SV40 early promoter (SV40 β gal) was used for in vivo studies in dogs and mice. The efficiency of gene transfer in vivo was evaluated by staining tissues for β galactosidase activity by standard methods. For both in vitro and in vivo experiments, the following proportion of components was used: DNA (1.8 μg) was mixed with LIPOFECTIN (8 μg) or LIPOFECTAMINE (12 μg) and adenovirus AD5 dl 312 (1.2× $10^{11}$ pfu) in 0.6 ml of reduced serum medium (OptiMEM 1). For in vitro experiments and the mouse in vivo experiments, the components were then incubated at 37° C. for 30 mins. For the dog experiments, the components were allowed to incubated within the artery.

For in vitro administration, DNA-lipid-adenovirus complexes were then added to cultured cells plated out in 12 well dishes (200 μl complex/well). Cells were washed twice with serum free medium just before addition of the DNA-lipid-adenovirus complexes. Cells were incubated with DNA-lipid-adenovirus complexes at 37° C. in 5% CO for 1 hr and then 1 ml of DMEM supplemented with 10% fetal bovine serum was added to each well. The medium was changed 24 hrs after transfection/infection and the cells were lysed and assayed for luciferase activity after 48–72 hrs post-transfection to assess the efficiency of gene transfer. Luciferase activity was assayed using a bioluminescence assay kit (Promega Corporation, Madison, Wis.) and a Moonlight 2010 Luminometer (Analytical Luminescence Laboratories). The total protein concentration of the target cells was measured by the Bradford method (reagent from BioRad Laboratories, Richmond, Calif.) with bovine serum albumin as a standard. Luciferase activity was expressed as relative light units per 50 microgram cell protein after subtracting background. Average standard deviations were around 15% of the mean value.

RESULTS

In Vitro Results

The efficiency of gene transfer was first tested using DNA-LIPOFECTIN/LIPOFECTAMINE-adenovirus complexes in a variety of cell types such as bovine aortic endothelial cells (BAECs), cardiac myocytes, HeLa cells and Cos 1 cells (see Table 1) at 4×$10^{10}$ pfu/well viral concentration. The protocol for gene transfer was then optimized in bovine aortic endothelial cells.

TABLE 1

| | Efficiencies of Gene Transfer in Different Cell Types | | | |
|---|---|---|---|---|
| | Luciferase Activity (Light Units/100 μg cell protein) | | | |
| | Lipofectin Alone | Lipofectin + AD5-DL 312 | Lipofectamine Alone | Lipofectamine + AD5-DL 312 |
| BAECs | 7 × $10^6$ | 4 × $10^7$ | 3 × $10^5$ | 3.4 × $10^8$ |
| HeLa Cells | 3.5 × $10^4$ | 5.9 × $10^5$ | 5.78 × $10^5$ | 1.76 × $10^6$ |

TABLE 1-continued

Efficiencies of Gene Transfer in Different Cell Types

| | Luciferase Activity (Light Units/100 μg cell protein) | | | |
|---|---|---|---|---|
| | Lipofectin Alone | Lipofectin + AD5-DL 312 | Lipofectamine Alone | Lipofectamine + AD5-DL 312 |
| Cardiac Myocytes | | | $2.43 \times 10^5$ | $9.5 \times 10^5$ |
| Cos 1 Cells | | | $4.24 \times 10^6$ | $9.98 \times 10^6$ |

Table 2 shows the effect of increasing the LIPOFECTAMINE concentration in the complex on the efficiency of gene transfer in bovine aortic endothelial cells (BAECs) at $4 \times 10^{10}$ pfu/well viral concentration. A LIPOFECTAMINE concentration of 8 μg/well gave optimal gene transfer.

TABLE 2

Effect of Increasing Lipofectamine Concentration on Efficiency of Gene Transfer in BAECs

| | Luciferase Activity Light Units/50 μg protein* | |
|---|---|---|
| Lipofectamine Conc. (μg/200 μl) | RSV-Luc + Lipofectamine + Adenovirus | RSV-Luc + Lipofectamine |
| 4 | $2.0 \times 10^8$ | $3.5 \times 10^6$ |
| 8 | $2.8 \times 10^8$ | $5.5 \times 10^6$ |
| 12 | $9.5 \times 10^7$ | $5.0 \times 10^6$ |
| 16 | $8.2 \times 10^7$ | $8.0 \times 10^6$ |

*averages of triplicate determinations

The effect of altering the concentration of adenovirus in the complex on the extent of gene delivery to BAECs was next examined. As shown in Table 3, at the highest concentration of adenovirus tested ($8 \times 10^{10}$ pfu/well), the efficiency of gene transfer using DNA-LIPOFECTAMINE-adenovirus complexes was over a thousand fold higher than the efficiency of gene transfer using DNA complexed with LIPOFECTAMINE alone (with LIPOFECTAMINE alone, luciferase activity was $1 \times 10^5$).

TABLE 3

Effect of Altering Adenovirus Concentration on Efficiency of Gene Transfer in BAECs

| Adenovirus Concentration (viral particles/well) | Luciferase Activity, Light Units/50 μg protein* |
|---|---|
| $4 \times 10^8$ | $1.6 \times 10^5$ |
| $1.3 \times 10^9$ | $1.5 \times 10^5$ |
| $4 \times 10^9$ | $2 \times 10^5$ |
| $1.5 \times 10^{10}$ | $2 \times 10^6$ |
| $4 \times 10^{10}$ | $2 \times 10^7$ |
| $8 \times 10^{10}$ | $1.4 \times 10^8$ |

*averages of triplicate determinations

In Vivo Results

The DNA-LIPOFECTIN/LIPOFECTAMINE-adenovirus complexes also showed efficient gene transfer in vivo. A plasmid construct with β-galactosidase as a reporter gene under control of the SV40 early promoter (SV40-β gal) was used for in vivo studies in dogs and mice. The efficiency of gene transfer was evaluated by staining tissues for β-galactosidase activity using standard methods. Femoral artery segments in anesthetized dogs were isolated using a cut-down procedure and infused with complexes of DNA-LIPOFECTIN-adenovirus or DNA-LIPOFECTIN alone in 3 ml of OptiMEM 1 under one atmosphere of pressure for a one-hour period (i.e., 15 μg plasmid DNA, 120 μl LIPOFECTIN, and $6 \times 10^{11}$ virions in a 3 ml volume). Blood flow through the femoral artery segments was thereafter reestablished and the dogs were subsequently allowed to recover. The femoral artery segments were harvested one week later and stained for β galactosidase activity (using Xgal stain with known procedures (Lim, K. and Chae, C., Biotechniques 7: 576–579 (1989) to assess the efficiency of gene transfer. Dog arteries that had been infused with SV40-β gal complexed with LIPOFECTIN and adenovirus showed efficient gene transfer of the β-galactosidase gene into the vessel wall. These arteries stained intensely blue. Control arteries infused with SV40-β gal complexed with LIPOFECTIN alone showed very little β-galactosidase activity whereas uninfused arteries did not show any detectable β-galactosidase activity.

To study the effects of direct injection of DNA-lipid-adenovirus complexes on gene transfer in vivo, mice were given intraventricular injections (0.2 ml) of SV40-β gal complexed with LIPOFECTAMINE and adenovirus. The mouse organs were dissected three days after injection and stained for β-galactosidase activity. Enhanced gene delivery into the liver, kidney and intestine in mice was observed by blue staining with Xgal as above.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of enhancing the delivery of a nucleic acid into a cell in vitro, comprising a. forming a complex comprising the nucleic acid linked via a cationic liposome to a virus; and b. administering the complex to the cell, thereby enhancing the delivery of the nucleic acid into the cell.

2. The method of claim 1, wherein the virus is replication deficient.

3. The method of claim 1, wherein the cationic liposome is LIPOFECTAMINE.

4. The method of claim 1, wherein the complex-forming step is performed at about 23° C. to about 42° C.

5. The method of claim 1, wherein the virus is an adenovirus.

6. The method of claim 5, wherein the adenovirus is strain Adenovirus 5 (AD5)-DL312.

7. The method of claim 1, wherein the nucleic acid functionally encodes a member selected from the group consisting of a peptide, polypeptide and protein.

8. The method of claim 1, wherein the nucleic acid functionally encodes an antisense RNA.

9. A method of enhancing the delivery of a nucleic acid into a cell in vitro comprising administering a complex comprising the nucleic acid linked via a cationic liposome to a replication deficient virus to the cell, thereby enhancing the delivery of the nucleic acid into the cell.

10. A complex comprising a nucleic acid linked via a cationic liposome to an adenovirus.

* * * * *